United States Patent
Kempf et al.

(10) Patent No.: US 9,040,819 B2
(45) Date of Patent: May 26, 2015

(54) IMPLANTABLE DEVICE HAVING AN INTEGRATED CERAMIC BUSHING

(75) Inventors: Mark Kempf, Inver Grove Heights, MN (US); Goran Pavlovic, Schaafheim (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 171 days.

(21) Appl. No.: 13/361,348

(22) Filed: Jan. 30, 2012

(65) Prior Publication Data

US 2012/0194981 A1    Aug. 2, 2012

Related U.S. Application Data

(60) Provisional application No. 61/438,014, filed on Jan. 31, 2011.

(30) Foreign Application Priority Data

Jan. 31, 2011  (DE) .................. 10 2011 009 860

(51) Int. Cl.
| | |
|---|---|
| H05K 5/06 | (2006.01) |
| A61N 1/375 | (2006.01) |
| H01R 13/52 | (2006.01) |
| H04R 25/00 | (2006.01) |

(52) U.S. Cl.
CPC ............... *A61N 1/375* (2013.01); *A61N 1/3754* (2013.01); *A61N 1/3756* (2013.01); *H01R 13/5224* (2013.01); *H04R 25/606* (2013.01); *H04R 2225/67* (2013.01)

(58) Field of Classification Search
USPC ..... 174/152 GM, 152 R, 153 A, 152 A, 50.5, 174/50.53, 50.52, 50.61, 11 BH; 361/679.01; 607/36, 37
See application file for complete search history.

(56) References Cited

U.S. PATENT DOCUMENTS

| | | | |
|---|---|---|---|
| 3,979,187 A | * | 9/1976 | Scherer ..................... 403/179 |
| 4,152,540 A | | 5/1979 | Duncan et al. |
| 4,217,137 A | | 8/1980 | Kraska et al. |

(Continued)

FOREIGN PATENT DOCUMENTS

| | | |
|---|---|---|
| DE | 69729719 | 7/2005 |
| DE | 102006054249 | 5/2008 |

(Continued)

OTHER PUBLICATIONS

Restriction Requirement for U.S. Appl. No. 13/361,322 mailed Nov. 14, 2013 (7 pages).

(Continued)

*Primary Examiner* — Angel R Estrada
*Assistant Examiner* — Dimary Lopez Cruz
(74) *Attorney, Agent, or Firm* — Dicke, Billig & Czaja, PLLC

(57) ABSTRACT

One aspect relates to a housing for an active implantable medical device, whereby the housing, at least parts thereof, includes an electrically insulating ceramic material, and has at least one electrically conductive conducting element, whereby the at least one conducting element is set up to establish at least one electrically conductive connection between an internal space of the housing and an external space.

One aspect provides the at least one conducting element to include at least one cermet, whereby the housing and the at least one conducting element are connected in a firmly bonded manner.

11 Claims, 6 Drawing Sheets

(56) References Cited

U.S. PATENT DOCUMENTS

| | | | |
|---|---|---|---|
| 4,315,054 A | 2/1982 | Sack et al. | |
| 4,354,964 A * | 10/1982 | Hing et al. | 252/512 |
| 4,488,673 A * | 12/1984 | Hopper, Jr. | 228/122.1 |
| 4,602,956 A | 7/1986 | Partlow et al. | |
| 4,678,868 A | 7/1987 | Kraska et al. | |
| 4,991,582 A * | 2/1991 | Byers et al. | 607/2 |
| 5,043,535 A | 8/1991 | Lin | |
| 5,515,604 A | 5/1996 | Horine et al. | |
| 5,738,270 A | 4/1998 | Malmgren | |
| 5,769,874 A * | 6/1998 | Dahlberg | 607/36 |
| 5,796,019 A | 8/1998 | Lupton et al. | |
| 5,861,714 A | 1/1999 | Wei et al. | |
| 5,870,272 A | 2/1999 | Seifried et al. | |
| 6,093,476 A | 7/2000 | Horiuchi et al. | |
| 6,414,835 B1 | 7/2002 | Wolf et al. | |
| 6,643,903 B2 | 11/2003 | Stevenson et al. | |
| 6,660,116 B2 | 12/2003 | Wolf et al. | |
| 6,999,818 B2 * | 2/2006 | Stevenson et al. | 607/37 |
| 7,035,076 B1 | 4/2006 | Stevenson | |
| 7,038,900 B2 | 5/2006 | Stevenson et al. | |
| 7,136,273 B2 | 11/2006 | Stevenson et al. | |
| 7,145,076 B2 | 12/2006 | Knappen et al. | |
| 7,174,219 B2 | 2/2007 | Wahlstrand et al. | |
| 7,174,223 B2 | 2/2007 | Dalton et al. | |
| 7,260,434 B1 | 8/2007 | Lim et al. | |
| 7,274,963 B2 | 9/2007 | Spadgenske | |
| 7,437,817 B2 | 10/2008 | Zhang et al. | |
| 7,480,988 B2 | 1/2009 | Ok et al. | |
| 7,502,217 B2 | 3/2009 | Zhao et al. | |
| 7,561,917 B2 | 7/2009 | Wegrzyn, III et al. | |
| 7,564,674 B2 | 7/2009 | Frysz et al. | |
| 7,630,768 B1 | 12/2009 | Coffed et al. | |
| 7,706,124 B2 | 4/2010 | Zhao et al. | |
| 7,720,538 B2 | 5/2010 | Janzig et al. | |
| 7,736,191 B1 | 6/2010 | Sochor | |
| 7,742,817 B2 | 6/2010 | Malinowski et al. | |
| 7,747,321 B2 | 6/2010 | Fischbach et al. | |
| 7,761,165 B1 | 7/2010 | He et al. | |
| 7,765,005 B2 | 7/2010 | Stevenson | |
| 7,794,256 B1 | 9/2010 | Sochor | |
| 7,901,761 B1 | 3/2011 | Jiang et al. | |
| 7,930,032 B2 | 4/2011 | Teske et al. | |
| 7,970,474 B2 | 6/2011 | Starke | |
| 7,989,080 B2 | 8/2011 | Greenberg et al. | |
| 8,000,804 B1 * | 8/2011 | Wessendorf et al. | 607/116 |
| 8,065,009 B2 | 11/2011 | Biggs | |
| 8,131,369 B2 | 3/2012 | Taylor et al. | |
| 8,163,397 B2 | 4/2012 | Ok et al. | |
| 8,179,658 B2 | 5/2012 | Brendel et al. | |
| 8,288,654 B2 | 10/2012 | Taylor et al. | |
| 8,346,362 B2 | 1/2013 | Kinney et al. | |
| 8,355,785 B1 | 1/2013 | Hammond et al. | |
| 8,391,983 B2 | 3/2013 | Lim | |
| 8,494,635 B2 | 7/2013 | Troetzschel et al. | |
| 8,497,435 B2 | 7/2013 | Nagata et al. | |
| 8,528,201 B2 | 9/2013 | Troetzschel et al. | |
| 8,552,311 B2 | 10/2013 | Koester et al. | |
| 8,656,736 B2 | 2/2014 | Terao | |
| 8,659,870 B2 | 2/2014 | Brendel et al. | |
| 8,742,268 B2 | 6/2014 | Reisinger et al. | |
| 8,825,162 B2 | 9/2014 | Reisinger | |
| 8,894,914 B2 | 11/2014 | Pavlovic | |
| 2001/0013756 A1 | 8/2001 | Mori et al. | |
| 2004/0116976 A1 | 6/2004 | Spadgenske | |
| 2004/0128016 A1 | 7/2004 | Stewart | |
| 2006/0247714 A1 | 11/2006 | Taylor et al. | |
| 2006/0259093 A1 | 11/2006 | Stevenson et al. | |
| 2007/0183118 A1 | 8/2007 | Fu et al. | |
| 2008/0119906 A1 | 5/2008 | Starke | |
| 2008/0203917 A1 | 8/2008 | Maya | |
| 2008/0269831 A1 | 10/2008 | Erickson | |
| 2009/0192578 A1 | 7/2009 | Biggs | |
| 2009/0281586 A1 | 11/2009 | Lim | |
| 2010/0023086 A1 | 1/2010 | Lim | |
| 2010/0109966 A1 * | 5/2010 | Mateychuk et al. | 343/841 |
| 2010/0258342 A1 | 10/2010 | Parker | |
| 2011/0034965 A1 | 2/2011 | Troetzschel et al. | |
| 2011/0034966 A1 | 2/2011 | Troetzschel et al. | |
| 2011/0186349 A1 | 8/2011 | Troetzschel et al. | |
| 2012/0127627 A1 | 5/2012 | Brendel et al. | |
| 2012/0193117 A1 | 8/2012 | Specht et al. | |
| 2012/0193118 A1 | 8/2012 | Kempf et al. | |
| 2012/0193119 A1 | 8/2012 | Kempf et al. | |
| 2012/0193125 A1 | 8/2012 | Pavlovic et al. | |
| 2012/0193141 A1 | 8/2012 | Reisinger et al. | |
| 2012/0194981 A1 | 8/2012 | Kempf et al. | |
| 2012/0197326 A1 | 8/2012 | Pavlovic | |
| 2012/0197327 A1 | 8/2012 | Specht | |
| 2012/0197335 A1 | 8/2012 | Reisinger | |
| 2012/0197368 A1 | 8/2012 | Reisinger | |
| 2012/0200011 A1 | 8/2012 | Pavlovic | |
| 2012/0203294 A1 | 8/2012 | Troetzschel | |
| 2014/0262494 A1 | 9/2014 | Reisinger et al. | |
| 2014/0368298 A1 | 12/2014 | Reisinger | |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |
| EP | 1754511 | 2/2007 |
| WO | 03073450 | 9/2003 |
| WO | 2004110555 | 12/2004 |
| WO | 2008103166 | 8/2008 |
| WO | 2010091435 | 8/2010 |

OTHER PUBLICATIONS

Office Action for U.S. Appl. No. 13/361,340 mailed Oct. 25, 2013 (20 pages).

Office Action for U.S. Appl. No. 13/361,355 mailed Aug. 7, 2013 (21 pages).

Restriction Requirement for U.S. Appl. No. 13/361,362 mailed Nov. 14, 2013 (7 pages).

Office Action for U.S. Appl. No. 13/361,370 mailed Oct. 29, 2013 (26 pages).

Restriction Requirement for U.S. Appl. No. 13/361,374 mailed Mar. 5, 2013 (6 pages).

Office Action for U.S. Appl. No. 13/361,374 mailed Oct. 4, 2013 (22 pages).

Restriction Requirement for U.S. Appl. No. 13/361,383 mailed Feb. 27, 2013 (6 pages).

Office Action for U.S. Appl. No. 13/361,383 mailed Nov. 13, 2013 (22 pages).

Restriction Requirement for U.S. Appl. No. 13/361,404 mailed Apr. 8, 2013 (6 pages).

Restriction Requirement for U.S. Appl. No. 13/361,404 mailed Oct. 9, 2013 (5 pages).

Notice of Allowance for U.S. Appl. No. 13/361,355 mailed Jan. 16, 2014 (18 pages).

Office Action for U.S. Appl. No. 13/361,322 mailed Feb. 19, 2014 (26 pages).

Office Action for U.S. Appl. No. 13/361,340 mailed Apr. 29, 2014 (18 pages).

Office Action for U.S. Appl. No. 13/361,362 mailed Feb. 19, 2014 (19 pages).

Office Action for U.S. Appl. No. 13/361,370 mailed May 14, 2014 (18 pages).

Office Action for U.S. Appl. No. 13/361,374 mailed May 1, 2014 (20 pages).

Notice of Allowance for U.S. Appl. No. 13/361,383 mailed Apr. 25, 2014 (18 pages).

(56) References Cited

OTHER PUBLICATIONS

Office Action for U.S. Appl. No. 13/361,388 mailed Feb. 11, 2014 (24 pages).
Office Action for U.S. Appl. No. 13/361,398 mailed Mar. 7, 2014 (26 pages).
Office Action for U.S. Appl. No. 13/361,404 mailed Feb. 27, 2014 (19 pages).
Restriction Requirement for U.S. Appl. No. 13/361,411 mailed Mar. 10, 2014 (7 pages).
Final Office Action for U.S. Appl. No. 13/361,322 mailed Sep. 9, 2014 (17 pages).
Final Office Action for U.S. Appl. No. 13/361,340 mailed Oct. 30, 2014 (21 pages).
Final Office Action for U.S. Appl. No. 13/361,362 mailed Sep. 9, 2014 (19 pages).
Final Office Action for U.S. Appl. No. 13/361,370 mailed Nov. 5, 2014 (19 pages).
Final Office Action for U.S. Appl. No. 13/361,374 mailed Nov. 10, 2014 (19 pages).
Final Office Action for U.S. Appl. No. 13/361,388 mailed Jul. 31, 2014 (32 pages).
Notice of Allowance for U.S. Appl. No. 13/361,398 mailed Jul. 25, 2014 (11 pages).
Final Office Action for U.S. Appl. No. 13/361,404 mailed Oct. 9, 2014 (12 pages).
Office Action for U.S. Appl. No. 13/361,411 mailed Aug. 1, 2014 (18 pages).

* cited by examiner

IMPLANTABLE DEVICE HAVING AN INTEGRATED CERAMIC BUSHING

CROSS-REFERENCE TO RELATED APPLICATIONS

This Non-Provisional patent application claims the benefit of the filing date of U.S. Provisional Patent Application Ser. No. 61/438,014, filed Jan. 31, 2011, entitled "IMPLANTABLE DEVICE HAVING AN INTEGRATED CERAMIC BUSHING," and this patent application also claims priority to German Patent Application No. DE 10 2011 009 860.7, filed on Jan. 31, 2011, and both of which are incorporated herein by reference.

This Patent Application is also related to patent application Ser. No. 13/361,322 filed on Jan. 30, 2012, entitled "CERAMIC BUSHING FOR AN IMPLANTABLE MEDICAL DEVICE"; patent application Ser. No. 13/361,340 filed on Jan. 30, 2012, entitled "DIRECTLY APPLICABLE ELECTRICAL BUSHING"; patent Application Ser. No. 13/361,355 filed on Jan. 30, 2012, entitled "HEAD PART FOR AN IMPLANTABLE MEDICAL DEVICE"; patent application Ser. No. 13/361,362 filed on Jan. 30, 2012, entitled "CERMET-CONTAINING BUSHING FOR AN IMPLANTABLE MEDICAL DEVICE HAVING A CONNECTING LAYER"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE" having US; patent application Ser. No. 13/361,374 filed on Jan. 30, 2012, entitled "CERAMIC BUSHING WITH FILTER"; patent application Ser. No. 13/361,383 filed on Jan. 30, 2012, entitled "CERAMIC BUSHING WITH INDUCTIVE FILTER"; patent application Ser. No. 13/361,388 filed on Jan. 30, 2012, entitled "CERAMIC BUSHING HAVING HIGH CONDUCTIVITY CONDUCTING ELEMENTS"; patent application Ser. No. 13/361,398 filed on Jan. 30, 2012, entitled "METHOD FOR THE MANUFACTURE OF A CERMET-CONTAINING BUSHING"; patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE"; and patent application Ser. No. 13/361,411 filed on Jan. 30, 2012, entitled "CERMET-CONTAINING BUSHING WITH HOLDING ELEMENT FOR AN IMPLANTABLE MEDICAL DEVICE".

BACKGROUND

One aspect relates to a housing of an active implantable medical device. Moreover, one aspect relates to a method for the manufacture of a housing for an electrical bushing for an implantable medical device.

The post-published document, DE 10 2009 035 972, discloses an electrical bushing for an implantable medical device having the features of the preamble of claim 1. Moreover, a use of at least one cermet-comprising conducting element in an electrical bushing for an implantable medical device and a method for the manufacture of an electrical bushing for an implantable medical device are disclosed.

A multitude of electrical bushings for various applications are known, examples including: U.S. Pat. No. 4,678,868, U.S. Pat. No. 7,564,674 B2, U.S. 2008/0119906 A1, U.S. Pat. No. 7,145,076 B2, U.S. Pat. No. 7,561,917, US 2007/0183118 A1, U.S. Pat. No. 7,260,434B1, U.S. Pat. No. 7,761,165, U.S. Pat. No. 7,742,817 B2, U.S. Pat. No. 7,736,191 B1, U.S. 2006/0259093 A1, U.S. Pat. No. 7,274,963 B2, US 2004116976 A1, U.S. Pat. No. 7,794,256, U.S. 2010/0023086 A1, U.S. Pat. No. 7,502,217 B2, U.S. Pat. No. 7,706,124 B2, U.S. Pat. No. 6,999,818 B2, EP 1754511 A2, U.S. Pat. No. 7,035,076, EP 1685874 A1, WO 03/073450 A1, U.S. Pat. No. 7,136,273, U.S. Pat. No. 7,765,005, WO 2008/103166 A1, U.S. 2008/0269831, U.S. Pat. No. 7,174,219 B2, WO 2004/110555 A1, U.S. Pat. No. 7,720,538 B2, WO 2010/091435, U.S. 2010/0258342 A1, U.S. 2001/0013756 A1, U.S. Pat. No. 4,315,054, DE 10 2008 021 064 A1, U.S. 2008/0119906 A1, U.S. Pat. No. 7,260,434 and EP 0877400.

DE 697 297 19 T2 describes an electrical bushing for an active implantable medical device—also called implantable device or therapeutic device. Electrical bushings of this type serve to establish an electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one of its sides. Said connection body includes a hollow space having at least one connection socket for connecting electrode leads. In this context, the connection socket includes electrical contacts in order to electrically connect the electrode leads to the control electronics on the interior of the housing of the implantable therapeutic device. Hermetic sealing with respect to a surrounding is an essential prerequisite of an electrical bushing of this type. Therefore, lead wires that are introduced into an electrically insulating base body, also called signal-transmission elements, through which the electrical signals are propagated, must be introduced into the base body such as to be free of gaps.

In this context, it has proven to be challenging that the lead wires generally are made of a metal and are introduced into a ceramic base body. In order to ensure durable connection between the two elements, the internal surface of a through-opening—also called openings—in the base body is metallized for attachment of the lead wires by soldering. However, the metallization in the through-opening has proven to be difficult to apply. Only expensive procedures ensure homogeneous metallization of the internal surface of the bore hole—and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally correspond

DETAILED DESCRIPTION

Figure 1:
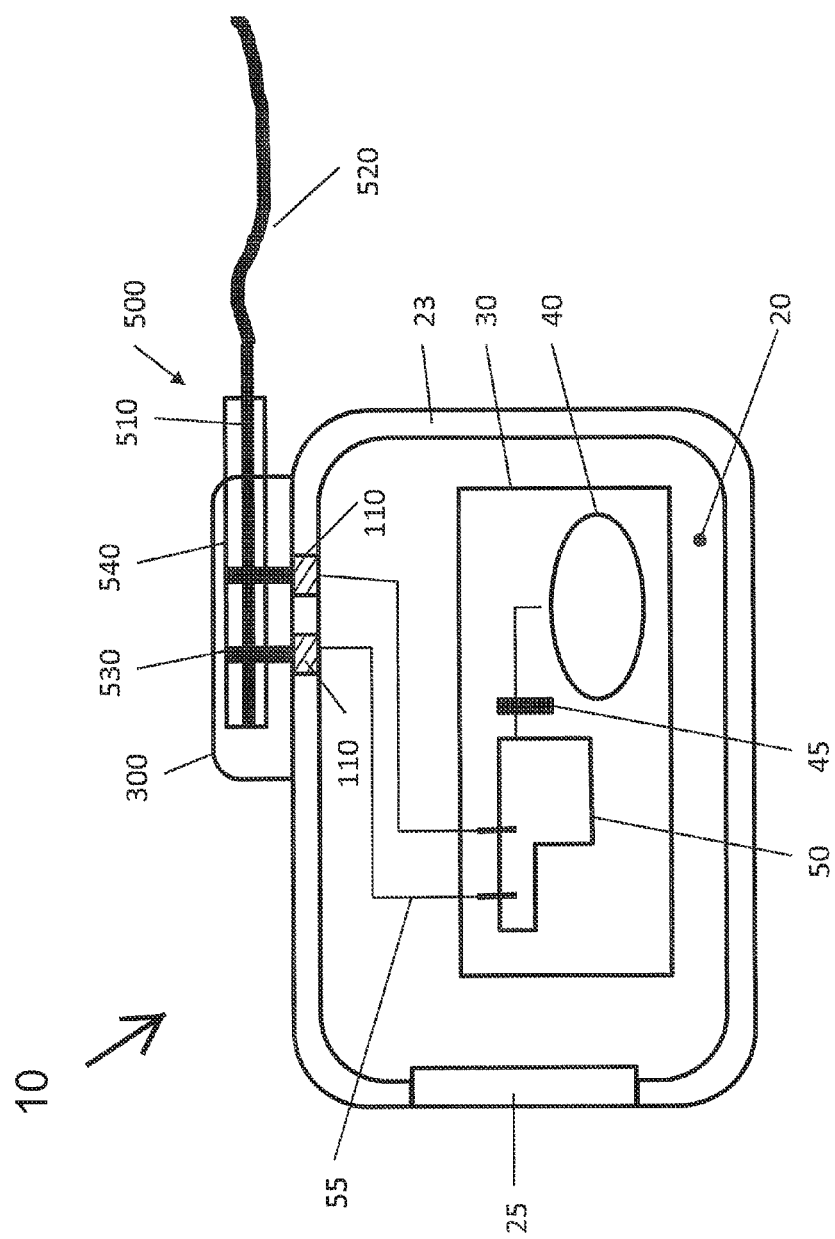
- FIG. 1 illustrates an active implantable medical device.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One aspect is to devise a housing of an implantable medical device which circumvents the disadvantages of known housings and/or medical devices of the type mentioned, at least in part. For example, a housing for an implantable medical device is to be proposed that is easy to manufacture, highly sealed, and, furthermore, enables external components to be connected easily.

A housing for an implantable medical device, an implantable medical device, a method for the manufacture of a housing of an implantable medical device having the features of the independent claims are proposed. Refinements of embodiments, which can be implemented alone or in combination, are specified in the dependent claims. Features and details that are described in the context of the housing or the method or the implantable medical device shall also apply in relation to the respective other devices or methods, and vice versa.

In summary, the following embodiments are proposed:

Embodiment 1: Housing for an active implantable medical device, whereby the housing, at least regions thereof, includes an electrically insulating ceramic material and has at least one electrically conductive conducting element, whereby the at least one conducting element is set up to establish at least one electrically conductive connection between an internal space of the housing and an external space, characterized in that the at least one conducting element includes at least one cermet, whereby the housing and the at least one conducting element are connected in a firmly bonded manner.

Embodiment 2: Housing according to the preceding embodiment, characterized in that the housing includes a ceramic region, whereby the ceramic region is provided through the electrically insulating ceramic material, whereby the ceramic region and the at least one conducting element are connected in a firmly bonded manner.

Embodiment 3: Housing according to the preceding embodiment, characterized in that the ceramic region is provided to be pocket-like in order to surround an electronic unit, at least regions thereof, of the active implantable medical device.

Embodiment 4: Housing according to any one of the preceding embodiments, characterized in that the conducting element is hermetically sealed with respect to the housing.

Embodiment 5: Housing according to any one of the preceding embodiments, characterized in that the conducting element is embedded in the housing.

Embodiment 6: Housing according to any one of the preceding embodiments, characterized in that the conducting element and the housing are connected through a firmly bonded, sintered connection.

Embodiment 7: Housing according to any one of the preceding embodiments, characterized in that the conducting element can be electrically contacted from the internal space.

Embodiment 8: Housing according to any one of the preceding embodiments, characterized in that the cermet includes at least one metallic component, whereby the metallic component is selected from the group consisting of: platinum; a platinum alloy; iridium; niobium; molybdenum; titanium; a titanium alloy; tantalum; a tantalum alloy; tungsten; a tungsten alloy; stainless steel; a cobalt-chromium alloy.

Embodiment 9: Housing according to any one of the preceding embodiments, characterized in that the cermet includes at least one ceramic component selected from the group consisting of: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of Ba (Zr, Ti)$O_3$, Ba (Ce, Ti)$O_3$, KNN, KNN—LiSbO$_3$, and KNN—LiTaO$_3$.

Embodiment 10: Housing according to any one of the preceding embodiments, characterized in that the housing includes a head part, whereby the head part, at least in part, is provided from an insulating composition of materials, such as from a plastic material.

Embodiment 11: Housing according to any one of the preceding embodiments, characterized in that the electrically insulating ceramic material is selected from the group consisting of: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of Ba (Zr, Ti)$O_3$, Ba (Ce, Ti)$O_3$, KNN, KNN—LiSbO$_3$, and KNN—LiTaO$_3$.

Embodiment 12: Housing according to any one of the preceding embodiments, characterized in that the medical device includes an antenna element, whereby the antenna element is set up to send and/or receive electromagnetic waves, for example, in that the antenna element includes a cermet, at least in part, for example, in that the housing and the antenna element include a firmly bonded, sintered connection, for example, in that the antenna element is connected to the conducting element in an electrically conductive manner.

Embodiment 13: Housing according to any one of the preceding embodiments, characterized in that the housing includes at least one filter element, whereby the filter element is connected to the at least one conducting element, for example, a filter element selected from the group consisting of: a high-pass filter, a low-pass filter, a band-pass filter.

Embodiment 14: Housing according to any one of the preceding embodiments, characterized in that the filter element includes at least one capacitor, whereby the capacitor includes electrodes and the electrodes are electrically connected in alternating manner to at least one of the conducting elements and the housing.

Embodiment 15: Housing according to any one of the preceding embodiments, characterized in that the housing includes a metallic, for example, band-like, housing rim, for example, in that the housing is closed in a hermetically sealed manner on the housing rim through a metallic lid.

Embodiment 16: Active implantable medical device, characterized in that the active implantable medical device includes a housing according to at least one of the preceding embodiments.

Embodiment 17: Implantable medical device according to any one of the preceding embodiments that are related to an implantable medical device, characterized in that the implantable medical device is selected from the group consisting of: an active implantable device for transmitting an electrical stimulation to a body tissue, for example, a muscle, a nerve, a brain region or a blood vessel; a cardiac pacemaker; an implantable defibrillator; a device against congestive heart failure; a hearing aid; a cochlea implant; a retina implant; a neuro-stimulator; a peripheral muscle stimulator; a drug pump, for example, an insulin pump; a ventricular aiding device; a spinal marrow stimulator; an implantable sensor system; an artificial heart; an incontinence device; a bone growth stimulator; a gastric pacemaker; a prosthetic device.

Embodiment 18: Method for the manufacture of a housing of an active implantable medical device, whereby the housing, at least regions thereof, includes an electrically insulating ceramic material and has at least one electrically conductive conducting element, whereby the at least one conducting element is set up to establish at least one electrically conductive connection between an internal space of the housing and an external space, characterized in that the method includes the following steps:
  forming a housing green compact from a ceramic material;
  generating at least one conducting element green compact from a cermet;
  joining the conducting element green compact and the housing green compact; and
  joint sintering of the housing green compact and the conducting element green compact in order to obtain a firmly bonded sintered connection between the housing and the conducting element.

Embodiment 19: Method according to the preceding embodiment that relates to a method, characterized in that the method includes the following steps:
  forming the housing green compact having a through-opening that extends through the housing green compact from a ceramic material;
  generating at least one conducting element green compact from a cermet;
  inserting the conducting element green compact into the through-opening of the housing green compact; and
  joint sintering of the housing green compact and the conducting element green compact in order to obtain a firmly bonded sintered connection between the housing and the conducting element.

Embodiment 20: Method according to the preceding embodiments that relate to a method, characterized in that the conducting element green compact and/or the housing green compact are sintered partly in a first sintering step prior to inserting the conducting element green compact into the through-opening.

Embodiment 21: Method according to any one of the preceding embodiments that relate to a method, characterized in that the forming and/or generating proceed in the scope of at least one of the following procedures: uniaxial pressing, cold isostatic pressing, hot isostatic pressing, injection molding or an extrusion procedure, for example, a co-extrusion procedure.

Embodiment 22: Method according to any one of the preceding embodiments that relate to a method, characterized in that, after completion of the sintering, at least one surface of the electrical conducting element is polished and contacted to a metallic pin or wire at least one site of the surface at which a conducting element is arranged.

The proposed housing is set up for use in an implantable medical device, that is, for application in an implantable medical device, whereby the implantable medical device can be provided, for example, as an active implantable medical device (AIMD) and, for example, as a therapeutic device.

As a general rule, the term, implantable medical device, shall include any device which is set up to perform at least one medical function and which can be introduced into a body tissue of a human or animal user. As a general rule, the medical function can include any function selected from the group consisting of a therapeutic function, a diagnostic function, and a surgical function. The medical function can, for example, include a function, in which at least one stimulus is exerted on the body tissue, for example, an electrical stimulus. Said stimulating function can be exerted, for example, by means of at least one stimulus generator and/or by means of at least one stimulus transmitter, for example by means of an actuator. However, other types of exerting a stimulus are also feasible as a matter of principle.

As a matter of principle, the term, active implantable medical device—also called AIMD—shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, includes at least one housing, for example, at least one hermetically sealed housing. The housing can in one embodiment enclose at least one electronics unit, for example a triggering and/or analytical electronics unit of the implantable medical device.

In one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element with respect to strains occurring during operation and/or upon handling, and/or provide protection to the functional element with respect to ambient influences such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can include at least one hollow space which can be closed fully or in part. However, alternatively, the internal space can be filled up fully or in part, for example by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing can, for example, be provided to be hermetically sealed such that, for example, the internal space, is hermetically sealed with respect to the external space. In one embodiment, the term, "hermetically sealed", can illustrate that moisture and/or gases cannot permeate through the hermetically sealed element at all or only to a minimal extent upon intended use for the common periods of time (for example 5-10 years). The so-called leak rate, which can be determined, for example, by leak tests, is a physical parameter that can describe, for example, a permeation of gases and/or moisture through a device, for example, through the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of present embodiments, said maximal permissible helium leak rates can, for example, be from $1\times10^{-8}$ atm*cm$^3$/sec to $1\times10^{-7}$ atm*cm$^3$/sec. In the scope of one embodiment, the term, "hermetically sealed", shall be understood, for example, to mean that the device to be tested (for example the housing) has a helium leak rate of less than $1\times10^{-7}$ atm*cm$^3$/sec. In one embodiment, the helium leak rate can be less than $1\times10^{-8}$ atm*cm$^3$/sec, for example, less than $1\times10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

The conducting element is set up to create at least one electrically conducting path that extends from the internal space of the housing to at least one external point or region outside the housing, for example, situated in the external space. Accordingly, this establishes, for example, an electrical connection to leads, electrodes, and sensors that are arranged outside the housing.

Common implantable medical devices are commonly provided with a housing, which can include, on one side, a head part, also called header or connecting body, that carries connection sockets for connection of leads, also called electrode leads. The connection sockets include, for example, electrical contacts that serve to electrically connect the leads to a control electronics unit on the interior of the housing of the medical device.

Due to the type of use of implantable medical devices, their hermetic sealing and biocompatibility are usually amongst the foremost requirements. The implantable medical device proposed herein according to one embodiment, for example, the housing, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device should be as impermeable as possible, for example, with respect to body fluids.

Moreover, strong electrical insulation between the at least one conducting element and the housing is to be ensured. In this context, the insulation resistance reached in one embodiment is at least several MOhm, for example, more than 20 MOhm, and the leakage currents reached can be small, for example, less than 10 pA. Moreover, in case multiple conducting elements are present, the crosstalk and electromagnetic coupling between the individual conducting elements in one embodiment are below the specified thresholds for medical applications.

The housing according to one embodiment is particularly well-suited for the above-mentioned applications. Moreover, the housing can also be used in other applications that are associated with special requirements with regard to biocompatibility, tight sealing, and stability with respect to corrosion.

The housing according to one embodiment can meet, for example, the above-mentioned tight sealing requirements and/or the above-mentioned insulation requirements.

As mentioned above, the housing according to one embodiment includes at least one electrically insulating ceramic region. In the scope of one embodiment, a ceramic region shall be understood to mean an element that serves, amongst other functions, a mechanical holding function, for example in that the ceramic region holds or carries the at least one conducting element either directly or indirectly. For example, the at least one conducting element can be embedded in the ceramic region directly or indirectly, fully or partly, for example, through a firmly bonded connection between the ceramic region and the conducting element and in one embodiment through co-sintering of the ceramic region and the conducting element. For example, the ceramic region can have at least one side facing the internal space and at least one side facing the external space and/or accessible from the external space.

Accordingly, the ceramic region can take the shape of a disc, for example a disc with a round, oval or polygonal base surface. Alternatively, the ceramic region can, for example, take a pocket-like or envelope-like shape. However, other designs are also feasible as a matter of principle.

As mentioned above, the ceramic region is provided to be electrically insulating. This means that the ceramic region, fully or at least regions thereof, is made from at least one electrically insulating material, for example, a ceramic material. For example, the at least one electrically insulating material can be arranged such that the at least one conducting element is electrically insulated with respect to the housing and/or, if multiple conducting elements are provided, that these are electrically insulated with respect to each other. In this context, an electrically insulating material shall be understood to mean a material with a resistivity of at least $10^2$ Ohm*m, for example, of at least $10^6$ Ohm*m, in one embodiment of at least $10^{10}$ Ohm*m, and in one embodiment of at least $10^{12}$ Ohm*m. For example, the ceramic region can be provided such that, as mentioned above, a flow of current between the conducting element and the housing and/or between further conducting elements of the housing and/or multiple conducting elements is prevented, at least largely, for example through the resistivity values between the conducting element(s) and/or the further elements of the housing other than the insulating ceramic region being implemented as specified above. For example, the ceramic region can include at least one ceramic material.

In this context, a conducting element or electrical conducting element shall generally be understood to mean an element set up to establish an electrical connection between at least two sites and/or at least two elements. For example, the conducting element can include one or more electrical conductors, for example metallic conductors. In the scope of one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side facing the internal space and/or on a side facing the external space or accessible from the external space, one or more connecting contacts, for example one or more plug-in connectors, for example one or more connecting contacts, which project from the ceramic region and/or the housing or can be electrically contacted through other means from the internal space and/or the external space. The conducting element can, for example, on the side of the ceramic region facing the internal space, end flush with the ceramic region and/or project from the ceramic region into the internal space or be connected to another element. Regardless of the design of the inside, this applies just as well to the side of the ceramic region facing the external space.

The at least one conducting element can be electrically connected within the ceramic region and/or on a side of the ceramic region that faces the internal space and/or on a side of the ceramic region that faces the external space, to one or more conductor elements. For example, one or more wires can be provided. The at least one conductor element can be manufactured, for example, fully or in part from at least one metallic material selected from the group consisting of: platinum; a platinum alloy; iridium; niobium; molybdenum; titanium; a titanium alloy; tantalum; a tantalum alloy; tungsten; a tungsten alloy; stainless steel; a cobalt-chromium alloy; gold; a gold alloy; silver; a silver alloy; copper; a copper alloy, aluminum or an aluminum alloy. Combinations of the specified materials and/or other materials are feasible just as well.

The at least one conducting element can establish the electrically conductive connection between the internal space and the external space in a variety of ways. For example, the conducting element can extend from at least one section of the conducting element that is arranged on the side of the housing and/or ceramic region facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other.

The electrically insulating ceramic region can support, as a bearing, and/or surround, at least in part, for example, the at least one conducting element. For example, the at least one conducting element can be embedded in the ceramic region fully or in part, for example in a firmly bonded manner. The at least one material of the housing, that is, the ceramic material of the housing, in one embodiment the at least one material of the ceramic region, should be biocompatible, as illustrated above, and should have sufficiently high insulation resistance. It has proven to be advantageous for the ceramic region according to one embodiment to include at least one ceramic material or to consist of at least one ceramic material. In one embodiment, the ceramic region includes one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate.

With regard to possible refinements of the cermet and/or metal materials and/or components that are used, reference shall be made to the embodiments specified above. Combinations of multiple possibilities specified above are conceivable as well. In this context, ZTA shall be understood to mean zirconium-toughened alumina (Zirkonia Toughened Alumina), that is, a material, in which zirconium oxide is embedded in an aluminum oxide matrix, for example 10-30% by volume zirconium dioxide in an aluminum oxide matrix. In this context, ATZ shall be understood to mean alumina-toughened zirconia, that is, a material, in which aluminum oxide is embedded in a zirconium oxide matrix, for example at a fraction of 10-30% by volume. Y-TZP shall be understood to mean yttrium-toughened zirconium oxide, that is, zirconium oxide comprising an yttrium fraction. KNN means potassium-sodium niobate.

The ceramic region and/or housing can, for example, be made fully or in part from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors with no ceramic fraction.

In the scope of one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added. The ceramic powder or powders of the cermet in one embodiment have a mean grain size of less than 10 μm, in one embodiment less than 5 μm, and in one embodiment less than 3 μm. The metallic powder or powders of the cermet in one embodiment have a mean grain size of less than 15 μm, in one embodiment less than 10 μm, and in one embodiment less than 5 μm. For production of a ceramic part of the housing and/or a ceramic region, for example, at least one ceramic powder can be used to which, for example, at least one binding agent and, if applicable, at least one solvent can be added. In this context, the ceramic powder(s) of the ceramic part of the housing in one embodiment has/have a mean grain size of less than 10 µm (1 µm corresponds to 1*10E-6 m), in one embodiment less than 5 µm, and in one embodiment less than 3 µm. For example, the median value or the d50 value of the grain size distribution is considered to be the mean grain size in this context. The d50 value corresponds to the value at which 50 percent of the grains of the ceramic powder and/or metallic powder are finer and 50% are coarser than the d50 value.

In the scope of one embodiment, a ceramic manufacturing method shall be understood to mean a procedure that includes at least one sintering process of at least one insulating and/or at least one electrically conductive material, for example, at least one ceramic material. As shall be explained in more detail below, said ceramic manufacturing method can, for example, include a forming for the manufacture of at least one form body, for example one ceramic green compact and/or at least one ceramic brown compact.

In the scope of one embodiment, a sintering or a sintering process shall generally be understood to mean a procedure for the manufacture of materials or work-pieces, in which powdered, for example, fine-grained, ceramic and/or metallic substances are heated and connected in the process. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, for example, at least 100 bar, or even at least 1000 bar. The process can proceed, for example, fully or partly, at temperatures below the melting temperature of the powdered materials, for example at temperatures of 700° C. to 1400° C. The process can be carried out, for example, fully or partly, in a tool and/or a mold such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

The housing according to one embodiment can be manufactured in a method comprising the following steps:

a. manufacturing the at least one housing, for example, a ceramic part of a housing, for example, a ceramic region, and inserting the at least one conducting element into the housing, for example, into the ceramic part of the housing, for example, into the ceramic region, in non-sintered or pre-sintered condition;

b. joint sintering of the housing, for example, of the ceramic part of the housing, for example, of the ceramic region, and the conducting element.

Accordingly, a sintered condition is understood to mean a condition of a work-piece, in which the work-piece has already undergone one or more steps of sintering. Accordingly, a non-sintered condition is understood to mean a condition, in which the work-piece has not yet undergone a step of sintering. In this condition, the work-piece can for example be present as a green compact. A pre-sintered condition shall be understood to mean a condition, in which the work-piece has already undergone at least one step of sintering or at least one part of a step of sintering, in which the work-piece has not been sintered completely though, that is, in which the work-piece can still be sintered further and can be sintered further through one or more steps of sintering. In this condition, the work-piece can be present, for example, as at least partial green compact, as brown compact or already as a ceramic body.

In the manufacture of the at least one conducting element and/or optionally in the manufacture of the housing, a method can be used, for example, in which at least one green compact is manufactured first, subsequently at least one brown compact is manufactured from said green compact, and subsequently the finished work-piece is manufactured from said brown compact through at least one sintering step. In this context, separate green compacts and/or separate brown compacts can be manufactured for the conducting element, and the housing, for example, the ceramic region, and can be connected subsequently. Alternatively, one or more common green compacts and/or brown compacts for the ceramic region and the conducting element can be produced. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, one or more binding materials. A brown compact shall be understood to mean a pre-form body which is generated from the green compact through at least one debinding step, for example at least one thermal and/or chemical debinding step, whereby the at least one binding agent and/or the at least one solvent is/are removed, at least partly, from the pre-form body in the debinding step.

The sintering process, for example, of a cermet, but of the ceramic region just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the conducting element, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate.

For the conducting element, the at least one metallic component of the cermet can include, for example, at least one of the following metals and/or an alloy based on at least one of the following metals: platinum, iridium, niobium, molybdenum, tantalum, tungsten, titanium, cobalt or zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content should be 25% by volume and more, in one embodiment 32% by volume, for example, more than 38% by volume, depending on which materials have been selected.

In the scope of one embodiment, the terms, "including a cermet," "comprising a cermet," and "cermet-containing", are used synonymously. Accordingly, the terms refer to the property of an element, being that the element contains cermet. This meaning also includes the variant of an embodiment in that the element, for example the conducting element, consists of a cermet, that is, is fully made of a cermet.

In one embodiment, both the at least one conducting element and the housing, for example, the ceramic region, can include one or more components which are or can be manufactured in a sintering procedure, or the at least one conducting element and the housing, for example, the ceramic region, are or can both be manufactured in a sintering procedure. For example, the housing, for example, the ceramic region, and the conducting element are or can be manufactured in a co-sintering procedure, that is, a procedure of simultaneous sintering of these elements. For example, the conducting element and the housing, for example, the ceramic region, each can include one or more ceramic components that are manufactured, and in one embodiment compacted, in the scope of at least one sintering procedure.

For example, a housing green compact, for example, a ceramic region green compact, can be manufactured from an insulating composition of materials. This can proceed, for example, by compressing the composition of materials in a mold. In this context, the insulating composition of materials is a powder mass, in which the powder particles illustrate at least minimal cohesion. In this context, the manufacture of a green compact proceeds, for example, through compressing powder masses and/or through forming followed by drying.

Said procedural steps can also be utilized to form at least one cermet-containing conducting element green compact. In this context, one embodiment can provide that the powder, which is compressed to form the conducting element green compact, is cermet-containing or consists of a cermet or includes at least one starting material for a cermet. Subsequently, the two green compacts—the housing green compact, for example, the ceramic region green compact, and the conducting element green compact—can be combined. The manufacture of the conducting element green compact and of the ceramic region green compact can just as well proceed simultaneously, for example, by multi-component injection molding, co-extrusion, etc., such that there is no longer a need to connect them subsequently.

While the green compacts are being sintered, they are in one embodiment subjected to a heat treatment below the melting temperature of the powder particles of the green compact. This usually leads to compaction of the material and thus to ensuing substantial reduction of the porosity and volume of the green compacts. Accordingly, one embodiment of the method is that the housing, for example, the ceramic region, and the conducting element can be sintered jointly. Accordingly, there is no longer a need to connect the two elements subsequently.

Through the sintering, the conducting element becomes connected to the housing, for example, the ceramic region, in one embodiment in a positive fit-type and/or non-positive fit-type and/or firmly bonded manner. In one embodiment, this achieves hermetic integration of the conducting element into the housing, for example, the ceramic region. In one embodiment, there is no longer a need for subsequent soldering or welding of the conducting element in the housing, for example, in the ceramic region. Rather, a hermetically sealing connection between the ceramic region and the conducting element is attained through the joint sintering and utilization of a cermet-containing green compact.

One refinement of the method according to one embodiment is characterized in that the sintering includes only partial sintering of the at least one optional housing green compact, for example, of the at least one optional ceramic region green compact, whereby said partial sintering can effect and/or include, for example, the debinding step described above. In one embodiment, the green compact is heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to its/their final size. In the scope of said variant of an embodiment, the green compact is sintered only partly in order to attain a certain stability to render the green compact easier to handle.

The starting material used for producing at least one conducting element green compact and/or at least one housing green compact, for example, ceramic region green compact, can, for example, be a dry powder or include a dry powder, whereby the dry powder is compressed in the dry state into a green compact and illustrates sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available, for example. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be shaped into a green compact without the application of high pressure.

In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the work-piece.

Thermoplastic and duroplastic polymers, waxes, thermogelling substances and/or surface-active substances, for example, can be used as binding agent—also called binder. In this context, these can be used alone or as binding agent mixtures of multiple components of this type. If individual elements or all elements of the housing (for example the at least one ceramic region green compact and/or the at least one conducting element green compact) are produced in the scope of an extrusion procedure, the composition of the binding agent should be such that the line of the elements extruded through the nozzle is sufficiently stable in shape for the shape defined by the nozzle to be maintained easily. Suitable binders, also called binding agents, are known to the person skilled in the art.

In contrast, the conducting element according to the prior art usually is a metal wire. A conducting element provided according to one embodiment with at least one cermet can be connected easily to other structural elements, since it is a composite of metal and ceramic material. Accordingly, one or more green compacts of both the conducting element and other structural elements, for example in the housing, for example, in the ceramic region, can be produced and subsequently subjected to a sintering process. Alternatively or in addition, at least one common green compact for multiple structural elements can be manufactured just as well. The resulting housing is not only particularly biocompatible and durable, but also possesses good hermetic sealing properties. Thus, usually no fissures or connecting sites still to be soldered arise between the conducting element and the housing, for example, the ceramic region. Rather, sintering results in the housing, for example, the ceramic region, and the conducting element becoming connected. A variant of an embodiment, therefore provides the at least one conducting element to consist of a cermet. In this variant of an embodiment, the conducting element includes not only components made of cermet, but is fully made of a cermet.

Generally, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing bearing element can proceed, for example, alike a process for homogeneous powders except that, at identical compression force, the metal is usually compacted more strongly than the ceramic material. Compared to sintered hard metals, the cermet-containing conducting element usually illustrates higher resistance to thermal shock and oxidation. As explained above, the ceramic components can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate. The at least one metallic component can include, for example, at least one of the following metals and/or an alloy based on at least one of the following metals: platinum, a platinum alloy, iridium, niobium, molybdenum, titanium, a titanium alloy, cobalt, zirconium, chromium, tantalum, a tantalum alloy, tungsten, a tungsten alloy.

There are various ways of connecting the lid according to one embodiment to the housing, for example, in a hermetically sealed manner. These options can also be combined with each other. Accordingly, one option is to directly connect the lid to the housing, for example in a positive fit-type manner and/or non-positive fit-type manner and/or firmly bonded manner. Moreover, the ceramic region can be connected to the housing rim in a variety of ways, for example, through at least one non-positive fit-type and/or positive fit-type and/or firmly bonded connection, in one embodiment through at least one firmly bonded connection, in one embodiment through a solder connection and/or a welded connection. In order to promote wetting of the ceramic region with solder, at least one metallization of the ceramic region can be provided, for example a metallization that is applied through at least one physical vapor deposition procedure, for example a sputtering procedure. Said metallization can, for example, include at least one metal selected from the group consisting of gold, titanium and chromium and/or at least one combination and/or at least one multiple layer comprising one or more of said metals.

As illustrated above, the at least one lid is provided for closing the at least one housing opening of the housing. Said at least one lid can be provided, for example, as metallic lid. The ceramic region and the housing rim can be connected to each other in a variety of ways, which can also be combined as a general rule. During the manufacture of the housing, the housing rim can first be connected to the ceramic region, or vice versa, for example. In said procedural steps, one or more non-positive fit-type and/or positive fit-type and/or firmly bonding connection procedures can be applied, whereby firmly bonding connection procedures are used in one embodiment.

As described above, the ceramic region can be provided to have one of various geometries. The ceramic region can, for example, be provided as an annular disc having, for example, a circular, oval or polygonal cross-section.

As before, the housing and the lid can be provided in a manner such that the lid can be positioned such as to be oriented unambiguously towards the housing, for example oriented in a self-centering manner to the at least one housing opening. This can be effected, as before, in that at least one part of the lid engages the housing opening in a perfect fit or with little tolerance, for example with a tolerance of less than 0.5 mm, for example, less than 0.2 mm, and in one embodiment less than 0.1 mm. Alternatively or in addition, the lid and/or the housing, for example, the housing rim, can just as well include one or more positioning aids which act in concert and, for example, interdigitate in order to ensure the unambiguous positioning described above. After the lid is positioned in the housing, the housing and the lid are connected in a firmly bonded manner in order to achieve the desired hermetical sealing.

According to another aspect, one embodiment proposes an implantable medical device having the features described above. Features and details that were described in the context of the housing and/or any of the methods shall also apply in relation to the implantable medical device, and vice versa. Moreover, the implantable medical device can further include, for example, at least one supply lead, which is also called "lead" or "leads" in English and can be set up to form an electrical connection to the conducting element, for example an electrical plug connection. The lead can, for example, include at least one plug element, for example at least one male and/or at least one female plug element, which can form an electrical plug-in connection with the plug connection element of the housing. This can, for example, be at least one male plug element which can be plugged into the at least one plug connection element, for example at least one plug element according to the IS-1 (ISO 5841-3), DF-1 (ISO 11318:1993) and/or IS-4 standard.

The housing includes the at least one housing opening. In one embodiment, said housing opening is surrounded by the housing rim. The housing rim thus forms, for example, a geometric and/or spatial border of the housing opening. This housing opening can be closed in a firmly bonded manner, for example, through a lid, for example, a metallic lid. The housing opening can basically be of any shape, for example a round, oval or polygonal shape. The housing can, for example, be assembled from multiple housing parts, for example from at least two housing shells, whereby, for example, the housing opening is accommodated in one of the housing parts or in at least two of the housing parts, for example in the form of cut-outs in the housing parts which complement each other to form the housing opening when the housing parts are joined. The housing can, for example, be manufactured fully or in part from a metallic material, in one embodiment from titanium or a titanium alloy.

Another aspect of one embodiment proposes a method for the manufacture of a housing, as illustrated above. Features and details that are described in the context of the housing and/or in the context of the implantable medical device shall also apply accordingly in relation to the method according to one embodiment, and vice versa. With regard to the steps of the method, reference shall be made to the description of the embodiments provided above. The methods can be carried out in the order of the procedural steps illustrated or in any other order. Moreover, procedural steps can also be carried out concurrently or overlapping in time. Moreover, the methods can include one or more additional procedural steps that are not illustrated.

The manufacturing of the housing, for example, of the ceramic region, and the insertion of the at least one conducting element into the housing, for example, the ceramic region, can proceed in various partial steps. Alternatively, said partial steps can be combined fully or in part such that the manufacturing of the ceramic region proceeds in such a manner that the at least one conducting element is already inserted into the ceramic region after the manufacture is completed. This means, for example, as illustrated above, that, in a ceramic manufacturing procedure for the housing, for example, for the ceramic region and for the at least one conducting element, separate green compacts can be produced initially, which are later connected to form a common green compact, which is then sintered, for example. Alternatively, at least one common green compact can be manufactured for the housing, for example, the ceramic region and the at least one conducting element. Accordingly, inserting the conducting element into the housing, for example, the ceramic region, is generally to be understood to mean a method, in which at least one conducting element is already inserted into the housing, for example, the ceramic region, after completion of the method. The at least one conducting element can, for example, be embedded, fully or in part, into the housing, for example, the ceramic region, and/or connected in a firmly bonded manner to the housing, for example, the ceramic region. However, other designs are also feasible as a matter of principle.

The proposed housing, the implantable medical device, and the methods according to various embodiments provide a large number of advantages as compared to known devices and methods of the specified type. Accordingly, a cost-efficient manufacturing method can be implemented which features high process reliability and low waste production at the same time. For example, according to one embodiment, the number of boundary surfaces can be reduced which allows the potential of errors to be generally reduced. The boundary surfaces being reduced reduces, for example, the ingress of moisture or body fluid. Simultaneously, the use of ceramic materials allows high mechanical stability and strong sealing against moisture, for example, body fluid, to be implemented. Accordingly, the proposed housings have a long service life. Simultaneously, unlike in conventional methods, a plurality of procedural steps can be combined and, optionally, automated in the scope of customary ceramic manufacturing procedures.

As part of the investigations, the following exemplary embodiment of a ceramic region according to one embodiment would be produced: In the first step, a cermet mass is produced from platinum (Pt) and aluminum oxide ($Al_2O_3$) containing 10% zirconium dioxide ($ZrO_2$). The following starting materials are used for this purpose:

40 vol. % Pt powder with a mean grain size of 10 µm, and
60 vol. % $Al_2O_3/ZrO_2$ powder with a relative $ZrO_2$ content of 10% and a mean grain size of 1 µm.

The two components were mixed, water and a binding agent were added, and the sample was homogenized through a kneading process. Analogous to the first step, a ceramic mass is produced in a second step from a powder with an $Al_2O_3$ content of 90% and a $ZrO_2$ content of 10%. The mean grain size was approx. 1 µm. As before, water and a binding agent were added to the ceramic powder and the sample was homogenized. In a third step, the ceramic mass made of aluminum oxide with a 10% zirconium dioxide content produced in step two was converted to the shape of a ceramic region. A cermet body, which was made from the cermet mass produced in step 1 and contained a mixture of platinum powder and aluminum oxide with a zirconium dioxide content of 10%, was introduced as green compact into an opening in the green compact of the ceramic region. Subsequently, the ceramic mass was compacted in the mold. Then the cermet and the ceramic component were subjected to debinding at 500° C. and the sintering was finished at 1650° C.

One aspect of the housing according to one embodiment is the integration of the conducting element into the housing. One embodiment provides that the conducting element is connected directly to the material of the housing. The housing material can, for example, be a ceramic material. The at least one conducting element can be inserted into said ceramic region of the housing in such a manner that the same a) is hermetically sealed with respect to the housing, and b) an electrically conductive connection between the internal space of the housing and the external space is enabled. Accordingly, the conducting element can be connected to the housing in such a manner that the conducting element hermetically closes a through-opening in the housing. In this context, it is advantageous for the conducting element to project, at least in part, into the through-opening and in one embodiment to fill the through-opening, at least in part. For example, the through-opening and/or the conducting element can be provided, at least in part, as an annular disc, for example, an annular disc having a round, oval or polygonal cross-section.

The housing according to one embodiment includes a ceramic material. Said ceramic material covers, for example, an area of the surface of the housing. Accordingly, a part of the housing is made of a ceramic material. Said part shall also be referred to as ceramic region hereinafter. The part of the housing consisting of a ceramic material—the ceramic region—can take any shape and design. For example, the conducting element can in one embodiment be supported in said ceramic region in a firmly bonded manner. The ceramic region can cover, for example, an area between 10% and 80% of an entire surface area of the housing. The ceramic region can take a round or oval shape and be arranged in one of the surfaces of the housing. The housing can, for example be assembled from multiple housing parts, for example from at least two housing shells, whereby, for example, the ceramic region can already be inserted in one of the housing parts or in at least two of the housing parts. Another refinement of the medical device according to one embodiment is characterized in that the housing includes a ceramic region that is made from the ceramic material, whereby the ceramic region of the housing and the at least one conducting element include a firmly bonded sintered connection, for example, in that the ceramic region is provided to be pocket-like in order to surround an electronics unit of the active implantable medical device, at least regions thereof. In one embodiment, the ceramic region includes at least 70% of the total surface area of the housing or of the medical device. In this context, the ceramic region surrounds the electronics unit in a pocket-like manner. Known ceramic material that can be used are characterized mainly by their biocompatibility. Accordingly, the medical device disclosed herein can be implanted long-term in the body of a patient without negative effects occurring. In one embodiment, the ceramic region was sintered from a ceramic slurry or powder.

In one embodiment, it has proven to be advantageous for the ceramic region to include or consist of a ceramic component that is identical to the ceramic component that is also used in the cermet. This enables a particularly homogeneous and even firmly bonded connection between the conducting element and the ceramic region of the housing to be established. Moreover, shrinking processes in the scope of sintering and/or the temperatures required for sintering do not adversely affect the firmly bonded sintered connection between the conducting element and the ceramic region of the housing.

Active implantable medical devices do not only serve for stimulation of body regions of a patient. Rather, medical devices nowadays include sensors that use leads to transmit information from the patient to the medical device. Information of this type is analyzed within the medical device. In order to provide a physician with access to said information it has proven to be advantageous in one embodiment that the housing includes an antenna element for sending and/or receiving electromagnetic waves, for example, if the antenna element is provided from a sintered cermet material or a sintered metallic material, whereby, for example, the housing and the antenna element include a firmly bonded sintered connection, for example, in that the antenna element is connected to the conducting element in an electrically conductive manner. The antenna element is part of a communication interface between the medical device, for example, the housing, and an external device. Electromagnetic waves induce currents and/or voltages in the antenna element that are analyzed through an electronics unit that is arranged within the medical device. Through this route, it is feasible, on the one hand, to send inquiries to the medical device. Simultaneously, the electronics unit of the medical device and/or the part of the communication interface formed by it can be designed such that electromagnetic waves can be emitted through the antenna element. This enables the medical device to send information about the patient's health from the inside of the patient's body to an external analytical unit. Moreover, it is feasible to utilize the antenna element for charging the battery of the medical device. This also utilizes electromagnetic waves to induce currents in the antenna element which then serve to charge the battery.

In one embodiment, it is an advantage of the antenna element disclosed herein that it can be provided from a cermet material or a metallic material that engages in a firmly bonded sintered connection to the housing. The antenna element is connected to the housing in a firmly bonded manner and is thus a part of the housing. In one embodiment, the housing, for example, the ceramic region of the housing, is electrically insulating. The ceramic region thus forms a Faraday cage and is permeable for electromagnetic waves. For this reason, the antenna element can be attached to an internal side of the housing and does not require an electrically conductive contact to the conducting element. Alternatively, the antenna element can be integrated into an external side of the ceramic region of the housing. In this case, it has proven advantageous in one embodiment for the antenna element to be connected to the at least one conducting element in an electrically conductive manner. This allows signals induced in the antenna element to flow through the conducting element into the inside of the housing and be processed through the electronics unit situated therein.

A refinement of the medical device according to one embodiment is characterized in that the housing includes multiple conducting elements. Having a plurality of conducting elements also creates a plurality of contact sites through which information can be conducted into the inside of the medical device. As illustrated, modern implantable devices enable not only electrical pulses to be emitted, but also include sensors on the leads. Each of said sensors and/or electrodes can utilize a corresponding conducting element. In one embodiment, the ceramic material, into which the conducting elements are sintered in a firmly bonded manner are electrically insulating. This ensures that there is no mutual interference of the individual conducting elements.

Medical devices are often not arranged at the site in the body, in which the generated electrical signal is meant to be effective. For this reason, active implantable medical devices often include leads which are connected to the housing on their distal ends and whose proximal end is situated in the corresponding body region to be stimulated. Due to their geometric size, the leads often act like antenna that couple to electromagnetic radiation. Electrical currents, for example, can thus be induced in the leads and flow from there into the electronics unit on the inside of the implantable device. This may possibly cause interference in the electronics unit. In order to reduce, for example, to prevent, said interference the housing can include at least one filter element, whereby the filter element is connected to the at least one conducting element, for example, a filter element selected from the group consisting of: a high-pass filter, a low-pass filter, a band-pass filter. In order to prevent said interference, another refinement of the medical device is characterized in that the medical device includes a filter element that is connected to the at least one conducting element in an electrically conductive manner in order to modify an electrical signal conducted by the at least one conducting element as a function of the signal's frequency and/or amplitude and/or phase. The electrical signal introduced into the lead from outside can, if applicable, interfere with the electronics unit of the implantable device. Accordingly, there is a need for a modification, for example, attenuation, of said electrical signal as a function of its frequency, amplitude or phase. To ensure this, it has proven to be advantageous in one embodiment that the filter element includes at least one capacitor, whereby the capacitor includes electrodes and the electrodes are electrically connected in alternating manner to at least one of the conducting elements and the housing. Integrating a filter element designed as illustrated allows, for example, each conducting element to exert an individual influence on interference signals, measuring signals or pulses. In this context, each conducting element can have a specific filter element assigned to it such that exertion of an influence or conduction with no influence is enabled as a function of the type of signal.

The housing of the medical device surrounds an electronics unit through which, for example, stimulatory signals can be generated. In a variant of an embodiment, the housing surrounds said electronics unit in a pocket-like manner. Since the housing is made from a ceramic material, same is generated separately in the scope of a sintering procedure. The board including the electronics unit is installed in the housing only after this procedure. The board cannot be installed earlier since the temperatures occurring during sintering are such that these may damage the electronics unit. Accordingly, the housing includes at least one housing opening through which the electronics unit is introduced into the housing. In order to seal said housing opening in a hermetical and lasting manner, it has proven to be advantageous in one embodiment that the housing includes a band-like housing rim, for example, that the housing is closed hermetically on the housing rim through a metallic lid. The band-like housing rim terminates a rim of the housing that is formed to be pocket-like. In one embodiment, the band-like housing rim consists of a biocompatible material, such as, for example, titanium, tantalum, niobium or an alloy of said metals. In a variant of the embodiment, the band-like housing rim is directly connected to the ceramic region. This can be effected through soldering or welding. In one embodiment, the ceramic region includes a metallization for connecting it to the housing rim, for example, in a firmly bonded manner. The advantage in one embodiment is that the housing thus generated can be directly tested for absence of leakage. The electronics unit is installed in the housing only thereafter and then connected to the conducting element(s). In order to hermetically seal the housing, there is a need for a metallic lid that is connected to the housing rim, for example, in a firmly bonded manner. One embodiment is advantageous as compared to known medical devices and/or housings in that no further elements need to be integrated into the metallic lid, such as, for example, an electrical bushing. Rather, the lid serves just to close the housing opening.

One embodiment also relates to a method for the manufacture of a housing of an active implantable medical device, whereby the housing, at least parts thereof, includes an electrically insulating ceramic material, and has at least one electrically conductive conducting element, whereby the at least one conducting element is set up to establish at least one electrically conductive connection between an internal space of the housing and an external space. The disadvantages of known manufacturing methods have already been discussed above. In one embodiment, the method described herein overcomes said disadvantages. One embodiment provides the method to include the following steps:

forming a housing green compact from a ceramic material;
generating at least one conducting element green compact from a cermet;
joining the conducting element green compact and the housing green compact; and
joint sintering of the housing green compact and the conducting element green compact in order to obtain a firmly bonded sintered connection between the housing and the conducting element.

Features and details that are described in the context of the active implantable medical device shall obviously also apply to the method for the manufacture of an active implantable medical device described here, and vice versa.

The scope of the method according to one embodiment includes a step of forming a housing green compact and a step of producing at least one conducting element green compact. Said steps can be carried out in parallel or in any sequential order. Moreover, the green compact formed or generated first can act in a support role in the subsequent steps of generating or forming the respective second green compact. The green compact is generated mainly through mechanical compaction of the ceramic material or cermet material, for example, of the powder or slurry. This often necessitates a mold, into which the slurry or powder is pressed. This aspect results in multiple variants of embodiments for the sequence of the individual procedural steps of the manufacturing method according to one embodiment:

Accordingly, the housing green compact, for example, the ceramic region green compact, can be formed first in the scope of one method. This can be effected, for example, by mechanical compression of the ceramic slurry and/or ceramic powder. The housing green compact, for example, the ceramic region green compact, can include a through-opening that extends through the green compact. The through-opening in the housing green compact, for example, the ceramic region green compact, can form a kind of mold for the second step of generating the conducting element green compact. The scope of this variant of an embodiment provides that the cermet slurry and/or the cermet powder and/or the metal component of the cermet is introduced, for example, dosed, into the through-opening, in one embodiment is dosed by means of a micro-dosing system, and compressed therein, for example, by hand. Accordingly, the through-opening serves as the mold that serves as the mold for mechanical compression of the cermet slurry and/or cermet powder. The conduction element green compact is generated by the compression inside the through-opening in the housing green compact, for example, the ceramic region green compact. In this variant of an embodiment, it is particularly expedient that the cermet slurry and/or the cermet powder is provided to be pasty, that is, as an, for example, doughy tough mass. A cermet-containing paste is easy and simple to introduce into the through-opening and to compress therein, for example, by hand. Introducing the cermet-containing paste—which includes a cermet slurry and/or a cermet powder—ensures, for example, that no fissures, gaps or other hollow spaces arise between the conducting element green compact and the housing green compact thus generated, which would possibly prevent a firmly bonded sintered connection between the conducting element and the housing from being established.

In another embodiment, the conducting element green compact is generated first. Subsequently, the conducting element green compact can be over-molded in one embodiment with a pasty ceramic slurry and/or ceramic powder. In this context, the conducting element green compact serves as a negative mold around which the housing green compact, for example, the ceramic region green compact, is built up.

In the scope of another variant of an embodiment, the housing green compact, for example, the ceramic region green compact, and the at least one conducting element green compact are produced separately. This can be effected by compression or any other known methods. In this context, the method can include the insertion of the at least one conducting element green compact into the at least one through-opening of the housing green compact, for example, into the ceramic region green compact. The mechanical stability of the green compacts allows them to be slid in, for example, allows the conducting element green compact to be slid into the through-opening. Subsequently, a firmly bonded connection is established between the conducting element green compact and the internal wall of the through-opening of the housing green compact, for example, the ceramic region green compact, in the scope of the later sintering. In order to promote this, the clearances between the conducting element green compact and the diameter of the through-opening caused by the shrinking process in the scope of the sintering should not exceed predetermined limits. This ensures that a firmly bonded connection between the conducting element green compact and the housing green compact, for example, the ceramic region green compact, can be established. It shall be noted in this context that a thermal treatment is not absolutely required in order to produce the green compact. Depending on the binding agent provided, mechanical pressure is sufficient to produce a green compact.

According to the scope of one embodiment, the step of combining the conducting element green compact and the housing green compact therefore does not necessarily include that both exist separately. One embodiment also includes that the conducting element green compact and/or the housing green compact is produced only during the step of combining in the scope of producing. for example, the first two of the methods described above suggest said interpretation of the procedural steps described herein.

One embodiment further provides the method to include the following steps:
forming the housing green compact having a through-opening that extends through the housing green compact from a ceramic material;
generating at least the conducting element green compact from a cermet;
inserting the conducting element green compact into the through-opening of the housing green compact; and
joint sintering of the housing green compact and the conducting element green compact in order to obtain a firmly bonded sintered connection between the housing and the conducting element.

The special feature of said variant of an embodiment of the method is that the conducting element green compact is being inserted into a through-opening of the housing green compact. Subsequently, the two green compacts are sintered jointly such that a firmly bonded connection between the housing and the conducting element arises. Accordingly, there is no need for further aids, such as solder, in order to attain a firmly bonded connection between the housing and the conducting element. Rather, both are connected directly to each other in a firmly bonded manner.

A variant of an embodiment is characterized in that the conducting element green compact and/or the housing green compact, for example, the ceramic region green compact, is/are partially sintered in a first sintering before inserting the conducting element green compact into the through-opening. The partial sintering achieves a compaction of the cermet powder or cermet slurry and/or ceramic powder or ceramic slurry. This is advantageous, in one embodiment, in that the green compacts are easier to handle and more resistant to external influences provided the materials are selected appropriately. However, the partial sintering is limited in that a firmly bonded connection still needs to be established in the scope of the final joint sintering of conducting element green compact and housing green compact. Accordingly, both green compacts cannot be completely sintered yet when the two elements are joining.

Another refinement is characterized in that the step of forming and/or generating and/or joining proceeds in the scope of at least one of the following procedures: uniaxial pressing, cold isostatic pressing, hot isostatic pressing, injection molding or an extrusion procedure, for example, a co-extrusion procedure.

FIG. 1 illustrates an active implantable medical device 10 according to one embodiment—also called implantable device or medical device. The medical device 10 includes a housing 20 in which an electronics unit 50 is integrated. The housing, at least regions thereof, is provided from a ceramic material and includes two electrically conductive conducting elements 110,110' in the exemplary embodiment illustrated. The conducting elements 110 extend through the housing 20. To render this feasible, the housing 20 includes a number of through-openings 440 that corresponds to the number of conducting elements. The electrical bushing 20 according to one embodiment allows helium leak rates of less than $1\times10^{-9}$ atm*cm$^3$/sec to be attained. Moreover, it withstands cleaning and sterilization processes.

The individual channels of the electronics unit 50 are connected to the individual conducting elements 110 through internal connecting elements 55. Said internal connecting elements 55 can be wires and/or sintered elements that are connected directly to the electronics unit 50. In case the implantable medical device 10 is a cardiac pacemaker, the electronics unit 50 is to trigger pulses which are conducted through a lead 500 to an electrode (not illustrated here) which in general is arranged to be situated right in the patient's heart muscle. In this location, the electrical pulse of the cardiac pacemaker can stimulate the heart muscle. The conducting elements 110 are part of said electrical lead that conducts the electrical pulse from the electronics unit 50 to the electrode. The actual lead 500 that is introduced into the patient's body includes a lead wire 520 that extends through parts of the patient and is connected to the electrode on its distal end. On the proximal end, the lead wire 520 is connected to a connector plug 510. Said connector plug 510 is supported, as in a bearing, in a receiving element 540. The receiving element 540 is part of a head part 300—also called header—that is connected to the housing 20 of the implantable device 10. Said head part 300 can be made from a plastic material. Multiple connecting sockets 530 are arranged inside the receiving element 540 and establish a non-positive type- and/or positive type-contact to the connecting plug 510. In addition, the connecting sockets 530 are connected through external connecting elements 60 to the conducting elements 110. On one inside within the housing 20, the conducting elements 110 are electrically connected through internal connecting elements 55 to the individual channels of the electronics unit 50 of the implantable device 10. Accordingly, an electrical pulse from the electronics unit 50 can be conducted through the internal connecting elements 55, through the conducting elements 110, the external connecting elements 60, and the connection socket 530 to the electrode and thus to the heart muscle.

The particularity according to one embodiment for overcoming the disadvantages mentioned above is that the conducting element 110,110' is made from a sintered cermet material. In order to attain hermetic sealing of the housing 20, the housing 20 and the conducting element 110,110' include a firmly bonded sintered connection. Both the region of the housing 20 made from ceramic material—also called ceramic region 23—and the conducting element 110,110' are sintered jointly. Thus is generated a media-tight firmly bonded connection between the two ceramic-containing materials of the conducting element 110,110' and of the housing 20.

Figure 2:
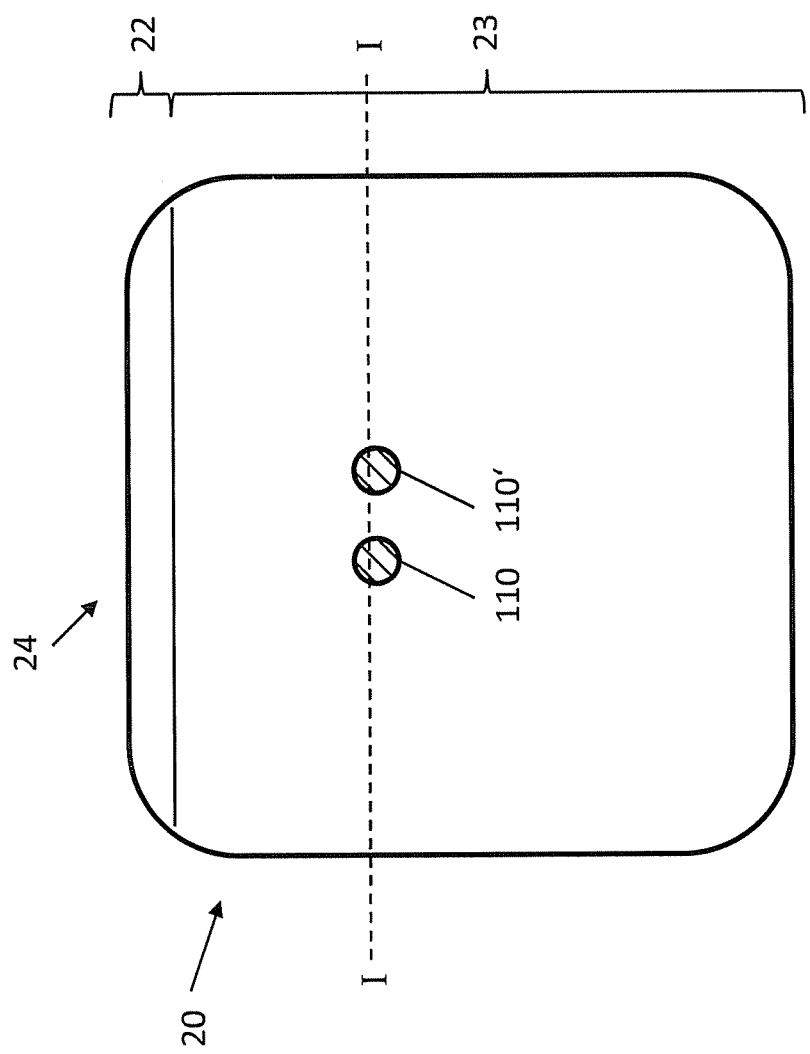
FIG. 2 illustrates a top view onto a housing of the medical device.
Figure 3:
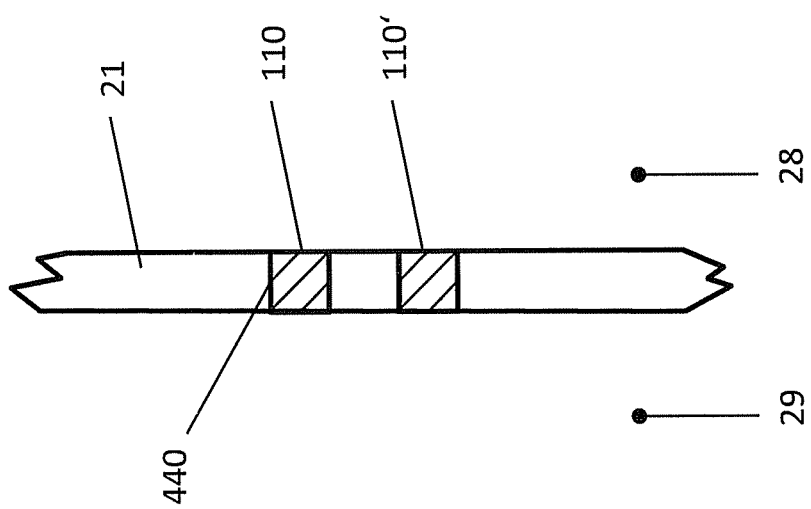
FIG. 3 illustrates a schematic view of a section through the housing according to FIG. 2 along the section line I/I.

FIGS. 2 and 3 illustrate the structure and the positioning of the conducting element 110,110' in the housing 20. FIG. 2 illustrates a housing 20. The housing 20 is provided on its upper end with a band-like housing rim 22 that surrounds a housing opening 24. The board 30 bearing the electronics unit can be inserted through said housing opening 24. The housing rim 22 that is designed like a collar is made of a metallic material, such as, for example, titanium. In the scope of a firmly bonded connection, the housing rim 22 is connected to the ceramic region 23. A housing 20 provided as described can be subjected to extensive quality tests in order to test the sealing with respect to environmental influences such as moisture. Deviating from the exemplary embodiment illustrated, the ceramic region 23 can just as well account for a smaller surface area as compared to the total surface area of the housing 20.

FIG. 3 illustrates a sectional drawing along sectional line I/I through the housing 20 from FIG. 2. The drawing includes just one half-shell 21 of the housing 20. In the scope of the method according to one embodiment for the manufacture of the medical device 10 described here, the housing 20 is produced from a housing green compact. The housing green compact, in turn, is produced from a ceramic slurry or a ceramic powder—for example, through methods that are known to the person skilled in the art. The green compact has a certain mechanical stability though not comparable yet to the final sintered product. The housing green compact includes a through-opening that is, for example, cylinder-like or rectangle-like. Said through-opening 440 extends fully through a wall of the housing 20 in at least one place—this being the half-shell 21 in FIG. 3. A conducting element green compact is to be inserted into said through-opening 440. After the final sintering, the through-opening 440 is at least partly filled by the conducting element 110,110'. Accordingly, the final housing 20 no longer includes a through-opening 440 in the sense that same is at least partly filled out by the conducting element 110,110' and has engaged into a hermetically sealed connection to the ceramic material of the housing 20.

In contrast to the non-conductive ceramic slurry or ceramic powder of the housing 20, the conducting element 110,110' is produced from a cermet slurry or a cermet powder that is electrically conductive. In a first step, the cermet slurry or the cermet powder are processed into a conducting element green compact through methods that are disclosed herein as well. The conducting element green compact is subsequently inserted into the through-opening 440 of the housing green compact. Then, the housing green compact and the conducting element green compact are sintered jointly. In the scope of joint sintering, a firmly bonded direct connection is established between the housing 20, which originates from the housing green compact, and the conducting element 110, 110', which originates from the conducting element green compact. As illustrated in FIG. 3, thus is produced an electrically conductive connection between an internal side 28 of the housing 20 and an external side 29 of the housing 20. Electrical signals can thus be conducted through the conducting element 110,110' into and/or out of the housing 20 without compromising the hermetic sealing thereof.

After final sintering of the ceramic region 23 of the housing 20, a firmly bonded contact is established between the ceramic region 23 and the metallic housing rim 22. Subsequently, the board bearing the electronics unit can be inserted into the housing and connected to the conducting elements 110,110'. A metallic lid 25 can then be used to hermetically close the inside of the implantable device 10. Said lid is connected to the metallic housing rim 22 in a firmly bonded manner through methods that are known to the person skilled in the art.

Figure 4:
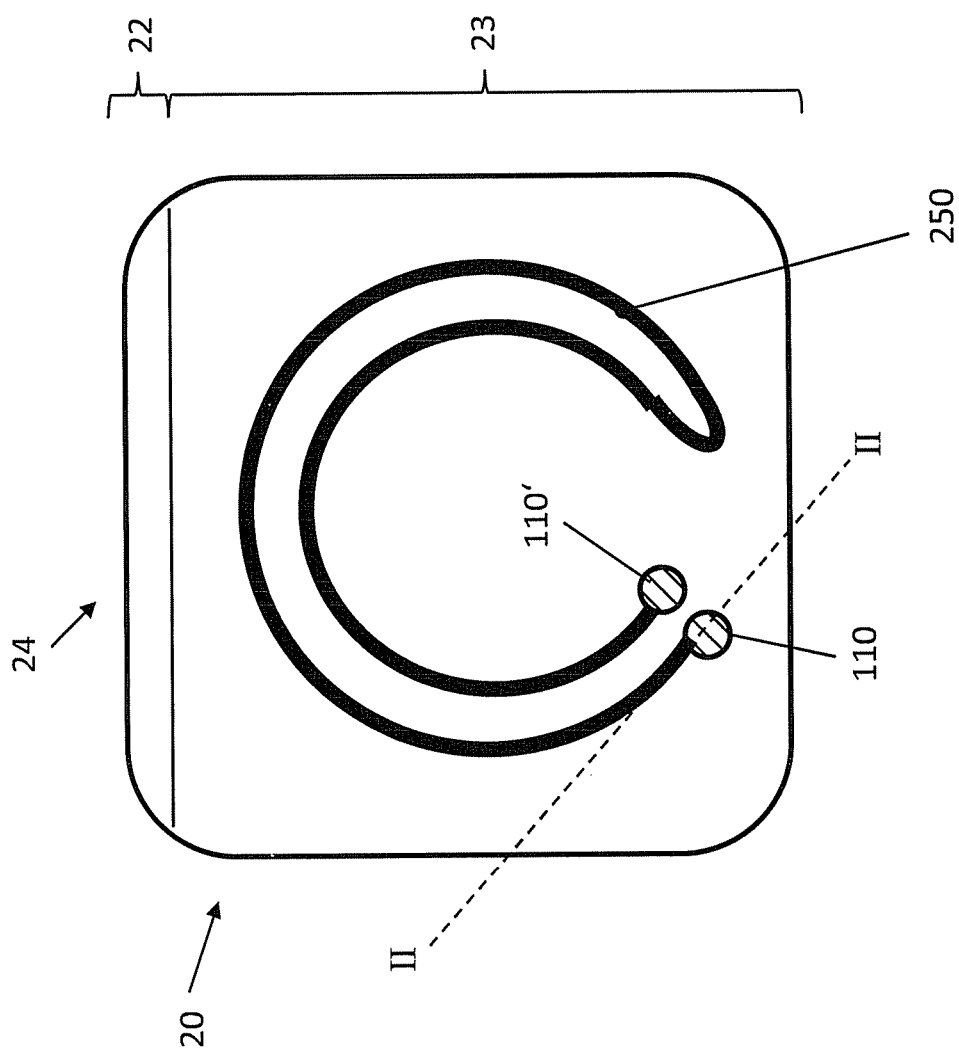
FIG. 4 illustrates another embodiment of the housing having an antenna element.
Figure 5:
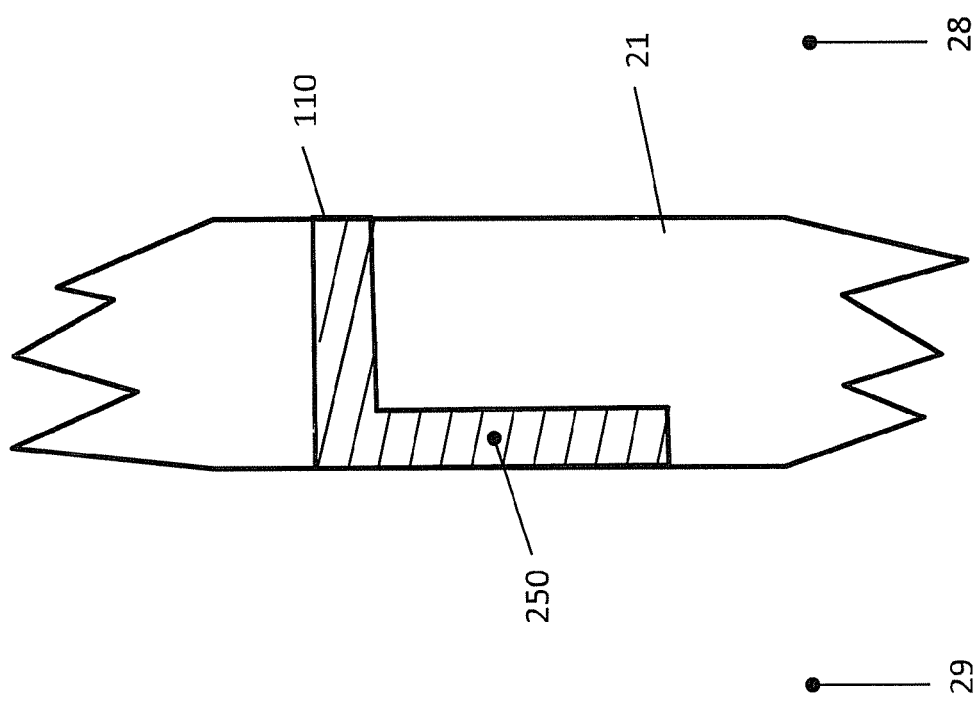
FIG. 5 illustrates a schematic view of a section through the housing according to FIG. 5 along the section line II/II.

FIG. 4 illustrates another variant of an embodiment of the housing 20 of the medical device 10 according to one embodiment. The housing 20 includes an antenna element 250 in addition to the conducting elements 110,110'. The antenna element 250 is electrically conductive and is provided from a sintered cermet material or a sintered metallic material. The purpose of the antenna element is to emit and/or absorb electromagnetic waves. Said electromagnetic waves can be radiated from outside at the housing 20 in order to send information and/or energy to the housing 20 and/or the electronics unit 50 of the implantable device 10. The antenna 250 is provided to be coil-like and is connected on each of its end to a conducting element 110,110'. FIG. 5 illustrates the arrangement of the antenna element 250 inside the housing 20.

FIG. 5 illustrates a schematic cross-section through the housing 20 according to FIG. 4 along the sectional line II/II. The antenna element 250 is introduced into the housing 20 from an external side 29. Moreover, one embodiment provides the housing 20 and the antenna element 250 to include a firmly bonded sintered connection. Accordingly, the antenna element 250 can be produced as an antenna element green compact to be inserted into a corresponding recess in the housing green compact and to be sintered jointly with same. Thus is generated a media-tight, direct, firmly bonded connection between the housing 20 and the antenna element 250. In the exemplary embodiment illustrated, the antenna element is arranged on an external surface of the housing 20. Accordingly, it can be seen from an external side 29. Signals that are absorbed by the antenna element 250 can be conducted through the conducting element 110 to an internal side 28 of the housing 20 and from there to an electronics unit. In a variant of an embodiment, the conducting element 110 and the antenna element 250 can be provided as the same part, for example, as the same part and made of the same material.

Figure 6:
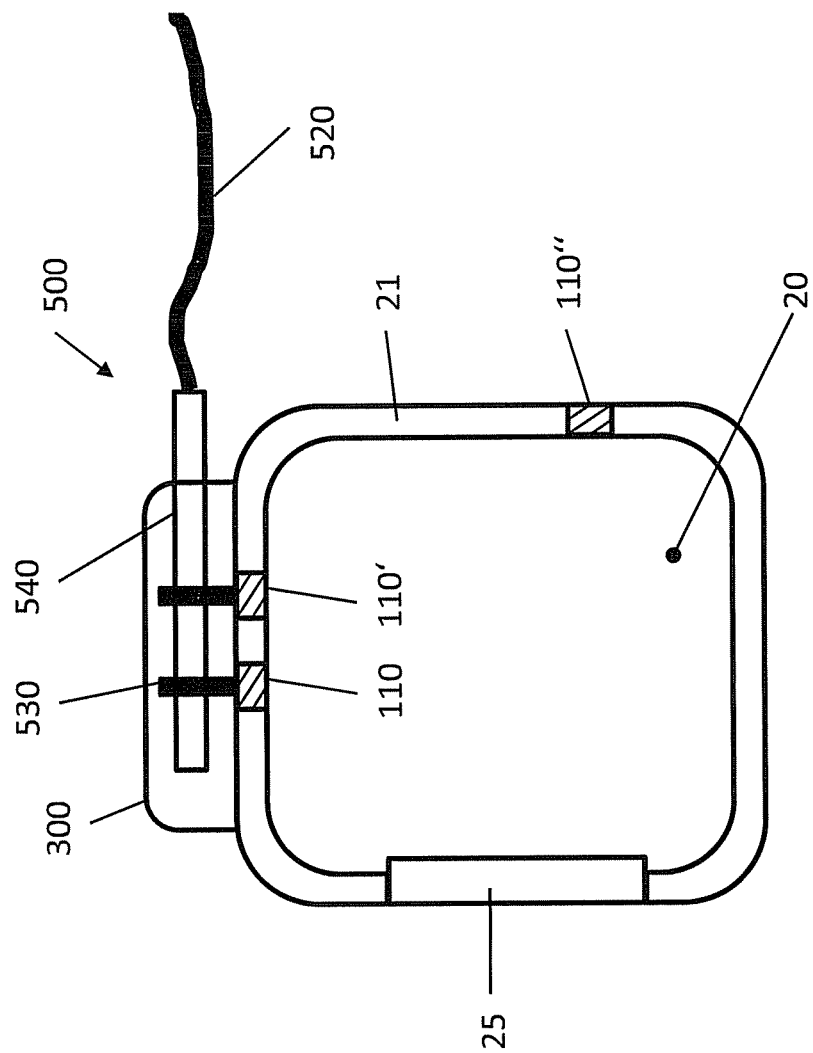
FIG. 6 illustrates another embodiment of the medical device.

FIG. 6 illustrates another variant of an embodiment of the implantable device 10 according to one embodiment with the housing 20. Here, the housing 20 includes two conducting elements 110 which are utilized to connect the lead 500. Moreover, the housing 20 is provided with another conducting element 110". Said conducting element 110" is not part of the electrical connection of the lead 500 to the electronics unit 50 of the implantable device 10. Rather, it is arranged in the housing 20 in such a manner that direct contact to a body tissue of a patient is established. Accordingly, the conducting element 110 can serve as a sensor or an electrode. The advantage according to one embodiment provided by the housing 20 disclosed herein is that the conducting element 110,110', 110" is integrated into the ceramic material of the housing 20 in a firmly bonded manner. Moreover, the conducting element is made from a cermet slurry or a cermet powder. A cermet is a multi-component material that is made up of a ceramic material in a metallic matrix. Since the material of the housing 20 and a part of the material of the cermet are ceramic materials, both can be connected to each other in a media-tight and firmly bonded manner in the scope of a common sintering process. Therefore, there is no need for any further intermediary steps in order to ensure the firmly bonded direct connection between the conducting element and the housing.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:
1. A housing for an active implantable medical device, comprising:
   a ceramic region comprising an electrically insulating ceramic material forming a pocket;
   at least one electrically conductive conducting element in the ceramic region; and
   a housing rim defining a housing opening;
   whereby electronics of the medical devices are insertable through the housing opening into the pocket;
   whereby a metallic lid is sealed to the housing rim thereby sealing the housing opening;
   whereby the at least one conducting element establishes at least one electrically conductive connection between an internal space of the housing and an external space;
   characterized in that the at least one conducting element comprises at least one cermet;
   whereby the housing and the at least one conducting element are coupled in a firmly bonded manner; and
   characterized in that the metallic lid consists only of metal and does not include the conducting element.
2. The housing according to claim 1, whereby the ceramic region and the at least one conducting element are connected in a firmly bonded manner.

3. The housing according to claim 1, characterized in that the conducting element is hermetically sealed with respect to the housing.

4. The housing according to claim 1, characterized in that the medical device comprises an antenna element, whereby the antenna element sends or receives electromagnetic waves, in that the antenna element comprises a cermet, at least in part, in that the housing and the antenna element comprise a firmly bonded, sintered connection, and in that the antenna element is connected to the conducting element in an electrically conductive manner.

5. The housing according to claim 1, characterized in that the housing is closed in a hermetically sealed manner on the housing rim through the metallic lid.

6. The housing according to claim 1, characterized in that conductive conducting element in the ceramic region is spaced apart from the metallic lid.

7. An active implantable medical device comprising:
a housing, the housing comprising:
an electrically insulating ceramic material; and
at least one electrically conductive conducting element;
whereby the at least one conducting element establishes at least one electrically conductive connection between an internal space of the housing and an external space;
characterized in that the at least one conducting element comprises at least one cermet comprising a ceramic material and a metallic material;
whereby the insulating ceramic component of the housing and the ceramic component of the cermet are identical such that the housing and the at least one conducting element are coupled in a firmly bonded manner; and
characterized in that the metallic lid does not include the conducting element.

8. The active implantable medical device according to claim 7, characterized in that the housing comprises a ceramic region, whereby the ceramic region is provided through the electrically insulating ceramic material, whereby the ceramic region and the at least one conducting element are connected in a firmly bonded manner.

9. The active implantable medical device according to claim 7, characterized in that the conducting element is hermetically sealed with respect to the housing.

10. The active implantable medical device according to claim 7, characterized in that the medical device comprises an antenna element, whereby the antenna element sends or receives electromagnetic waves, in that the antenna element comprises a cermet, at least in part, in that the housing and the antenna element comprise a firmly bonded, sintered connection, and in that the antenna element is connected to the conducting element in an electrically conductive manner.

11. The active implantable medical device according to claim 7, characterized in that the housing comprises a metallic housing rim, in that the housing is closed in a hermetically sealed manner on the housing rim through a metallic lid.

* * * * *